(12) United States Patent  
D'Augustine et al.

(10) Patent No.: US 6,416,779 B1
(45) Date of Patent: *Jul. 9, 2002

(54) DEVICE AND METHOD FOR INTRAVAGINAL OR TRANSVAGINAL TREATMENT OF FUNGAL, BACTERIAL, VIRAL OR PARASITIC INFECTIONS

(75) Inventors: Merida A. D'Augustine; James H. Liu; Donald C. Harrison, all of Cincinnati, OH (US)

(73) Assignee: UMD, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/613,441

(22) Filed: Jul. 11, 2000

Related U.S. Application Data

(63) Continuation-in-part of application No. 09/249,963, filed on Feb. 12, 1999, now Pat. No. 6,086,909, which is a continuation-in-part of application No. 09/079,897, filed on May 15, 1998, now Pat. No. 6,197,327.
(60) Provisional application No. 60/049,325, filed on Jun. 11, 1997.

(51) Int. Cl.[7] ............................. A61F 6/08; A61F 6/06; A61F 6/14
(52) U.S. Cl. ................... 424/430; 424/431; 424/432; 424/434; 424/443; 424/433
(58) Field of Search ................ 424/430, 431, 424/432, 434, 443, 433

(56) References Cited

U.S. PATENT DOCUMENTS

| | | | |
|---|---|---|---|
| 3,852,155 A | 12/1974 | Moore | 195/1.8 |
| 4,016,270 A | 4/1977 | Pharriss et al. | 424/242 |
| 4,073,743 A | 2/1978 | Midler, Jr. et al. | 252/309 |
| 4,250,166 A | 2/1981 | Mackawa et al. | 424/81 |
| 4,318,405 A | 3/1982 | Sneider | 128/263 |
| 4,405,323 A | 9/1983 | Auerbach | 604/285 |
| 4,540,581 A | 9/1985 | Nair et al. | 514/415 |
| 4,560,549 A | 12/1985 | Ritchey | 424/18 |
| 4,615,697 A | 10/1986 | Robinson | 604/890 |
| 4,789,667 A | 12/1988 | Makino et al. | 514/161 |
| 4,863,725 A | 9/1989 | Deckner et al. | 424/81 |
| 4,983,392 A | 1/1991 | Robinson | 424/427 |
| 5,026,543 A | 6/1991 | Rijke | 424/81 |
| 5,084,277 A | 1/1992 | Greco et al. | 424/433 |
| 5,185,146 A | 2/1993 | Altenburger | 424/89 |
| 5,192,802 A | 3/1993 | Rencher | 514/535 |
| 5,201,326 A | 4/1993 | Kubicki et al. | 128/832 |
| 5,246,697 A | 9/1993 | Conte et al. | 424/78.03 |
| 5,273,521 A | 12/1993 | Peller et al. | 604/13 |
| 5,275,820 A | 1/1994 | Change | 424/426 |
| 5,314,915 A | 5/1994 | Rencher | 514/535 |
| 5,330,761 A | 7/1994 | Baichwal | 424/469 |
| 5,362,498 A | 11/1994 | Aiache | 424/435 |
| 5,393,528 A | 2/1995 | Staab | 424/436 |
| 5,527,534 A | 6/1996 | Myhling | 424/430 |
| 5,742,525 A * | 4/1998 | Larsen | 424/616 |
| 5,788,980 A | 8/1998 | Nabahi | 424/430 |
| 5,985,319 A * | 11/1999 | Embil et al. | 424/450 |
| 6,086,909 A * | 7/2000 | Harrison et al. | 424/430 |

FOREIGN PATENT DOCUMENTS

| WO | WO 87/02576 | 5/1987 | A61F/5/46 |
|---|---|---|---|
| WO | WO 89/03207 | 4/1989 | A61K/9/50 |

* cited by examiner

Primary Examiner—Thurman K. Page
Assistant Examiner—Rachel M. Bennett
(74) Attorney, Agent, or Firm—Hana Verny

(57) ABSTRACT

Devices, methods, and compositions for treating vaginal fungal, bacterial, viral and parasitic infections by intravaginal or transvaginal administration of therapeutic and/or palliative antifungal, antibacterial, antiviral or parasiticidal drugs to the vagina or to the uterus.

18 Claims, 6 Drawing Sheets

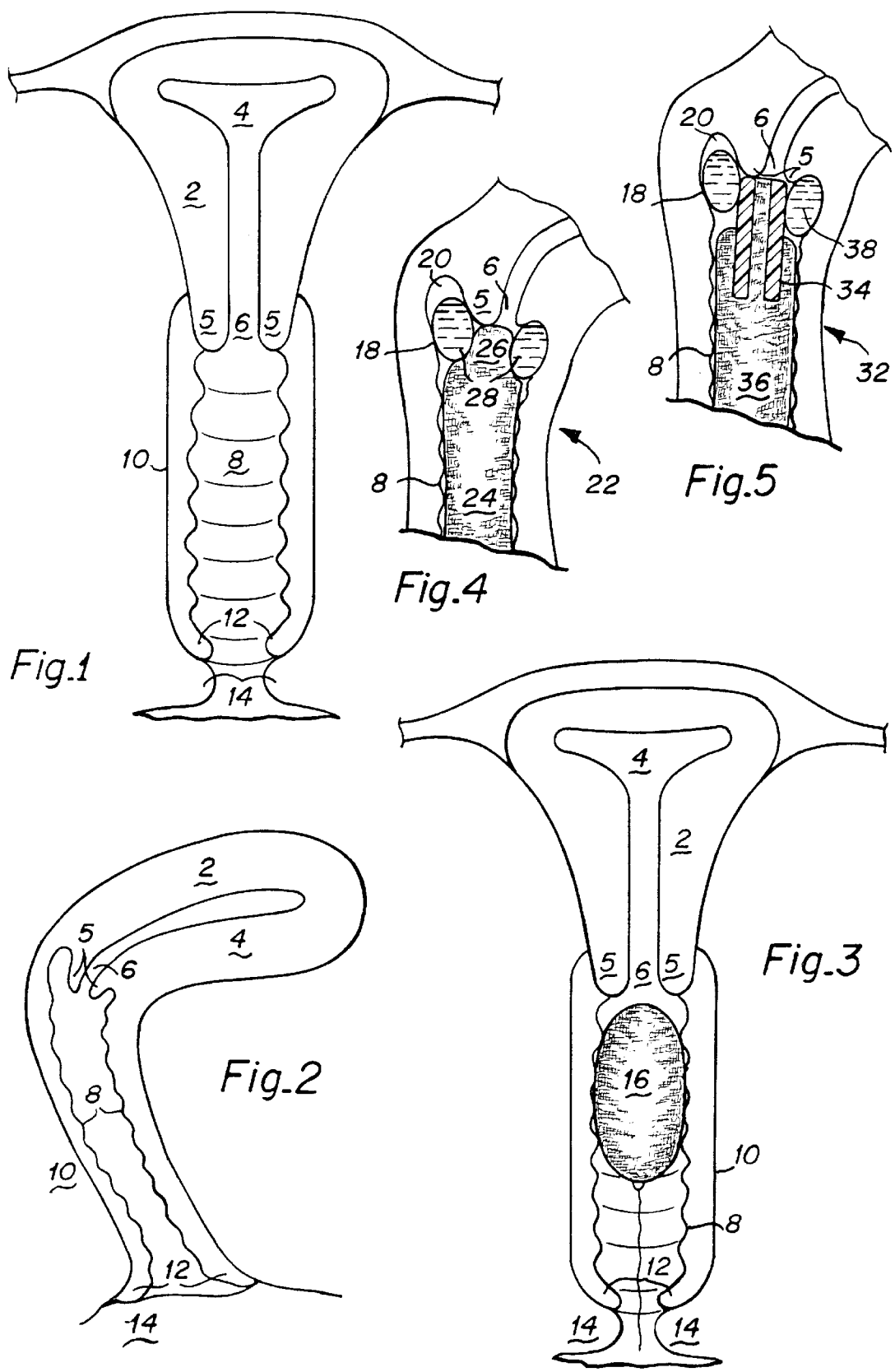

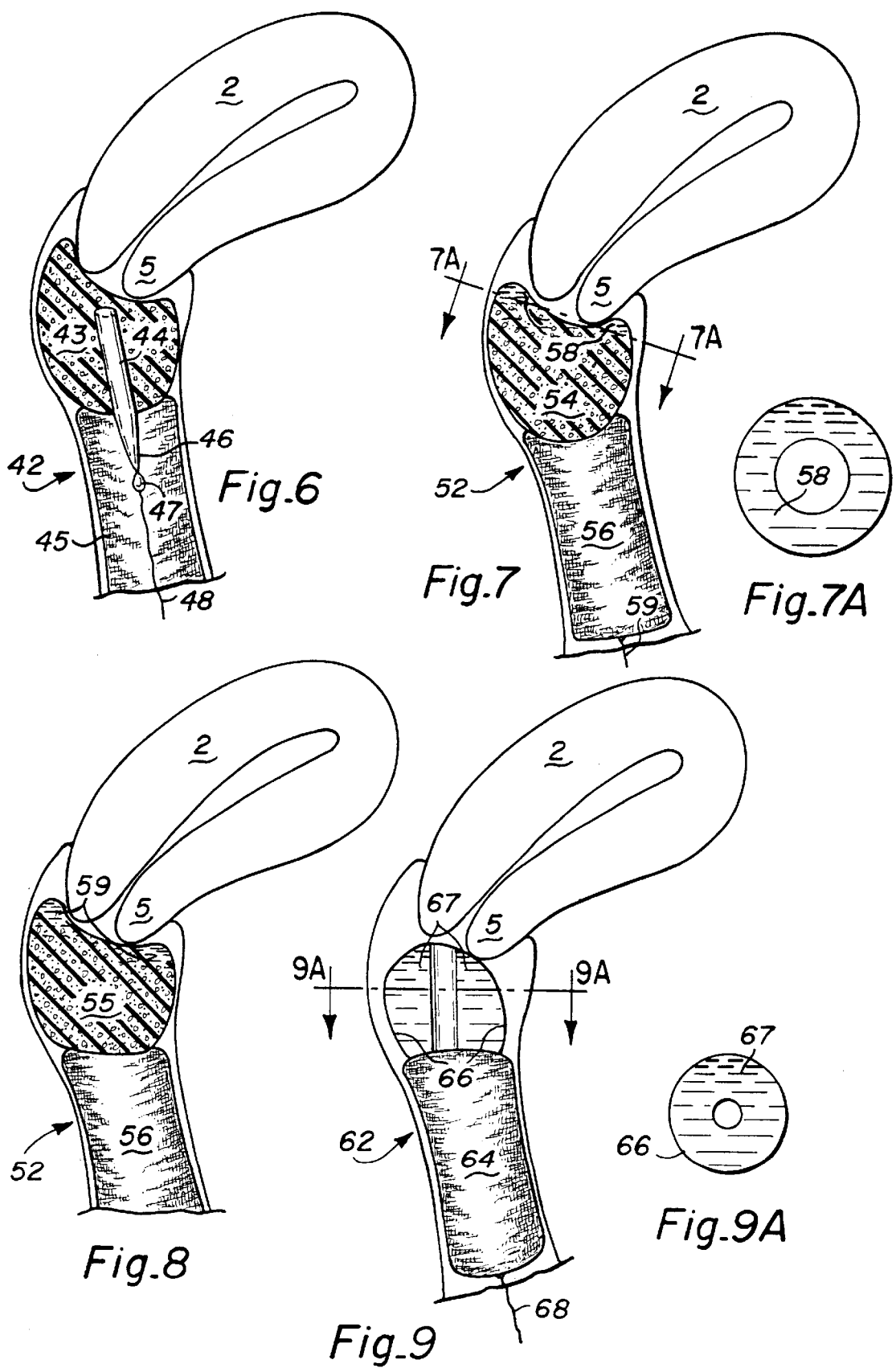

DEVICE AND METHOD FOR INTRAVAGINAL OR TRANSVAGINAL TREATMENT OF FUNGAL, BACTERIAL, VIRAL OR PARASITIC INFECTIONS

RELATIONSHIP TO COPENDING APPLICATIONS

This application is a continuation-in-part of application Ser. No. 09/249,963, filed Feb. 12, 1999, issued as U.S. Pat. No. 6,086,909 on Jul. 11, 2000, which is a continuation-in-part of the U.S. patent application Ser. No. 09/079,897, filed on May 15, 1998, issued as U.S. Pat. No. 6,197,327, which claims priority from the commonly assigned provisional application Ser. No. 60/049,325, filed Jun. 11, 1997, under 35 U.S.C. §111(b).

BACKGROUND OF THE INVENTION

1. Field of the Invention

The present invention concerns devices, methods and compositions for intravaginal or transvaginal treatment of vaginal fungal, bacterial, viral or parasitic infections by administration of therapeutic and/or palliative antifungal, antibacterial, antiviral or parasiticidal drugs intravaginally to the vaginal mucosa or transvaginally to the uterus and general blood circulation. In particular, the invention concerns a targeted site delivery of drugs to the vagina for treatment of fungal, viral, bacterial or parasitic infection using a medicated intravaginal device. The medicated intravaginal device allows delivery of the drug into the vagina and provides a continuous contact with the vaginal mucosa and epithelium thereby asserting its therapeutic effect topically on the vaginal mucosa and/or transvaginally into the uterus or to the systemic circulation. The medicated intravaginal device of the invention permits administration of lower concentrations of the drug than those needed for systemic treatment, prevents leaking of the drug out of the vagina, provides better and longer bioavailability of the drug by maintaining the continuous contact with the vaginal mucosa and improves sanitary conditions of vaginal treatments.

2. Background and Related Disclosures

Vaginitis, vaginosis and other conditions caused by yeast, bacteria, viruses or parasites are common medical problems in women that are associated with substantial discomfort, particularly due to a copious pathologic discharge which is often accompanied by irritation, pruritus, odor or urinary symptoms. Several commonly known infections, such as yeast infection, bacterial vaginosis, trichomonas, chlamydia or gonococcal infections are common causes of the vaginal discharge.

Currently available treatments of vaginitis or other vaginal conditions include a systemic oral administration therapy or topically intravaginally introduced intravaginal creams, intravaginal suppositories, ointments or tablets which, in order to release the drug from these formulations, melt or dissolve in the vagina. The drug and other formulation components which are released during this process leak from the vagina creating unsanitary conditions and discomfort and also, more importantly, resulting in delivery of unpredictable amount of the drug.

One of the most recent studies, described in *J. Reprod. Med.*, 44:543 (1999), reports that at this time, oral therapy is still preferred over intravaginal therapy. This is no doubt due to problems associated with vaginally delivered pharmaceutical agents. These problems include a discharge and leaking from the vagina which occurs during the treatment period, loss of drug due to such leaking, uncertainty of the amount of the drug delivered and general feeling of non-sanitary conditions which occur during such treatment.

Systemic treatment of vaginitis, which seems to be currently preferred, however, leads to the use of much higher doses of drugs which are potentially dangerous and typically cause severe secondary symptoms and complications. For example, local treatment of vaginal candiditis, a yeast infection, requires the use of antifungal drugs, such as nystatin, clotrimazole, miconazole and such similar drugs, administered as a cream via applicator, as suppository, or as a tablet, at bedtime. Due to a leakage encountered with such local treatment, once-a-day at bedtime treatment is recommended.

Once-a-day local administration of the drug does not provide continuous level of drug to treat the vaginal conditions, to deliver the drug to the uterus or to the general blood circulation and may lead to development of drug-resistance.

Thus it would be advantageous to have available treatment which would provide a continuous and predictable delivery of the drug to the vaginal mucosa and/or which would deliver the drug transvaginally into uterus or to the general blood circulation to avoid a necessity to administer the drug in high doses and to avoid a deactivation of the drug by the gastrointestinal tract.

Transvaginal delivery of a drug via a vaginal device has been disclosed by inventors and is described in the U.S. Pat. No. 6,197,327 and in U.S. Pat. No. 6,086,909, both incorporated herein by reference.

It is therefore a primary object of this invention to provide a device, composition and a method for topical and local treatment of vaginal infections by providing an intravaginal device comprising an antifungal, antibacterial, antiviral, trichomonicidal or parasiticidal agents incorporated within the device. The method of the invention provides a treatment of vaginal candidiasis, bacterial vaginosis, genital herpes, chlamydiosis, trichomoniasis, gonorrhea and human papilloma virus which eliminates the need for systemic treatment, which permits continuous delivery of the drug to the vaginal mucosa locally and topically and, where appropriate, which permits transvaginal delivery of the drug to the uterus and/or to the general circulation.

All references, patents and patent applications cited herein are hereby incorporated by reference in their entirety.

SUMMARY OF THE INVENTION

One aspect of the present invention is a device, method and a composition for intravaginal or transvaginal delivery of effective doses of a pharmaceutical agent to the vagina, uterus or to the general blood circulation.

Another aspect of this invention is a medicated device containing a pharmaceutical agent suitable for treatment of vulvovaginal candidiasis, bacterial vaginosis, chlamydiosis, genital herpes, gonorrhea, human papilloma virus or trichomoniasis.

Yet another aspect of this invention is an intravaginal device for intravaginal delivery of a pharmaceutical agent selected from the group consisting of an intravaginal tampon, tampon-like device, intravaginal ring, intravaginal pessary, intravaginal sponge, intravaginal tablet or intravaginal suppository comprising a pharmaceutical agent formulated as a cream, lotion, foam, ointment, solution or gel incorporated within said device.

Still yet another aspect of this invention is an intravaginal device for delivering an effective amount of a pharmaceutical agent to the vaginal mucosa for treating a human female suffering from vaginitis, vaginosis or other infection or disease, wherein the device is an absorbent intravaginal tampon or tampon-like device comprising a proximal and a distal end wherein a means for delivery of the pharmaceutical agent to the vaginal epithelium and/or to the uterus through the vaginal mucosa is situated at the distal end of the tampon and wherein a means for conveying fluid discharged from the vagina is situated near the proximal end of the tampon thereby preventing contact and dilution of the agent with the fluid.

Still another aspect of this invention is a method for treating a human female patient suffering from vaginal or uterine infections, conditions or diseases, said method comprising contacting the vaginal epithelium of the female with a pharmaceutical agent selected from the group consisting of an antifungal agent, antibacterial agent, parasiticidal agent, antiviral agent and/or trichomonicidal agent.

Still another aspect of this invention is a composition comprising an antifungal, antibacterial, antiviral, parasiticidal or trichomonicidal agent alone or in combination with other therapeutical agents in admixture with a biocompatible, pharmaceutically acceptable excipient for application of said agent(s) to the vaginal epithelium or for the transvaginal delivery through the vaginal mucosa, said agent(s) present in an amount sufficient to attain a therapeutically effective amount of the agent(s) in the vagina or in the uterus upon insertion of intravaginal device comprising said composition incorporated thereto.

Still yet another aspect of this invention is a pharmaceutically acceptable composition, in dosage unit form, for intravaginal or transvaginal delivery to a human female via a device of the invention, said composition comprising a combination of an effective amount of a pharmaceutical agent with components promoting adhesion of the composition to the vaginal mucosa or promoting a transport of the drug through the vaginal mucosa to the uterus.

BRIEF DESCRIPTION OF THE DRAWINGS

FIG. 1 is a cross-sectional representation of a portion of the female reproductive organs including the uterus and vagina in the upright orientation.

FIG. 2 is a cross-sectional side view representation of a portion of the female reproductive organs including the uterus and vagina.

FIG. 3 is the representation of FIG. 1 showing placement of a vaginal device of a drug delivery system according to the present invention.

FIG. 4 is a cross-sectional side view representation of the vaginal area adjacent the cervix showing placement of a tampon device incorporating an annular delivery composition.

FIG. 5 is the representation of FIG. 2 showing placement of a tampon device according to the present invention.

FIG. 6 is the representation of FIG. 2 showing placement of a tampon device incorporating a distal porous foam section.

FIG. 7 is the representation of FIG. 2 showing placement of a tampon device incorporating a distal porous foam cup.

FIG. 7A is a cross-sectional view of the embodiment shown in FIG. 7, taken in the direction indicated by the arrows labeled 7A in FIG. 7.

FIG. 8 is an alternate arrangement to the one shown in FIG. 7 in which medication is contained in the entire porous foam cup.

FIG. 9 is the representation of FIG. 2 showing placement of a tampon device incorporating a distal suppository or gel capsule.

FIG. 9A is a cross-sectional view of the embodiment shown in FIG. 9, taken in the direction indicated by the arrows labeled 9A in FIG. 9.

DEFINITIONS

Figures 10, 10A:
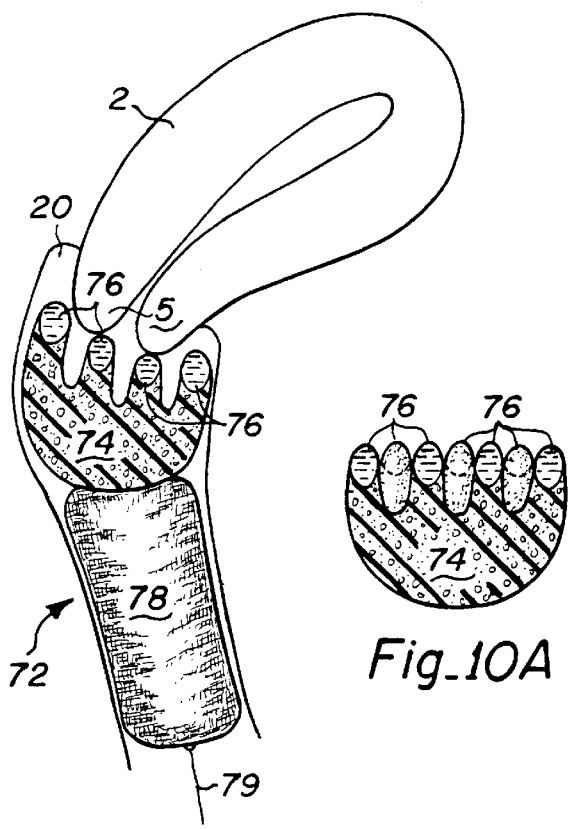
FIG. 10 is the representation of FIG. 2 showing placement of a tampon device incorporating a distal foam cup having "fingers."
FIG. 10A is a side view of the distal porous foam cup.

As used herein,

"Drug" or "agent" means a therapeutically effective compound suitable for treatment of infections, conditions or diseases described herein.

DETAILED DESCRIPTION OF THE INVENTION

This invention concerns intravaginal and transvaginal treatments for fungal, bacterial, viral or parasitic diseases. These vaginal infections and diseases typically result in a pathological discharge from the vagina causing an affected female patient a great discomfort.

Treatments of various vaginal infections, such as vaginitis, vaginal candidiasis, bacterial vaginosis, or other diseases and conditions, such as human papilloma virus, gonorrhea, chlamydiosis, genital herpes, or trichomoniasis are limited due to severe side-effects observed with systemic administration of pharmaceutical agents used for their treatment. Moreover, when treated systemically, these medical conditions may require administration of higher drug levels than necessary and when treated locally intravaginally, these treatments lead to uncertain dosage, leaking from the vagina, discomfort and unsanitary conditions.

The invention concerns a discovery that these problems could be overcome by focusing the delivery of drug therapy directly to the vaginal mucosa and epithelium using an intravaginal device comprising a specially formulated composition containing an appropriate therapeutical agent, which composition promotes adhesion of the drug released from the device to the vaginal epithelium for intravaginal delivery and treatment of surface vaginal infection, or which promote transvaginal delivery of the drug through vaginal mucosa to the uterus or to the general circulation for treatment of cervical or uterine infections and conditions. By contacting the vaginal mucosa with the drugs incorporated into the device according to this invention, greatly increased concentrations of therapeutic drugs suitable for treating vaginal infections are obtained.

The drug is delivered intravaginally either to the vaginal epithelium for treatment of topical vaginal conditions, such as, for example for treatment of candidiasis, trichomoniasis or genital herpes, or transvaginally through the vaginal mucosa to the uterus for treatment of uterine or cervical conditions, such as, for example, for treatment of cervicitis caused by chlamydia or gonococcus, or to the systemic circulation for treatment of conditions, such as gonorrheal infection of urethra, rectum, or pharynx, or for treatment of underlying systemic disease, such as, for example, herpes virus or human immunodeficiency virus (HIV).

Two delivery routes, that is the intravaginal and transvaginal route, may be combined by formulating the drug for both vaginal topical and transvaginal delivery and the drug may thus be conveniently delivered to the vaginal epithelium as well as, at the same time, transvaginally to the uterus, cervix and/or to the circulation. Additionally, more than one drug may be present in the composition permitting intravaginal treatment of vaginal epithelium with one drug, for example, acyclovir, for treatment of herpes, and at the same time, transvaginal treatment of the primary disease, for example, AZT for treatment of AIDS patients.

The transvaginal delivery of the drugs into the uterus is based on the discovery described in U.S. Pat. No. 6,127,327 and U.S. Pat. No. 6,086,909, incorporated herein by reference, that a special circulation exists between the vagina and the uterus, which permits preferential uptake of the drug into the uterus when the drug is administered intravaginally or transvaginally using a device of the invention. Such device is, preferably, a medicated tampon, vaginal ring, medicated pessary, medicated cervical cup, medicated tablet, medicated suppository or any other device, as described below, which is suitable for intravaginal insertion.

I. Treatment of Vaginal and Uterine Infections and Other Conditions

Treatment of vaginitis, vaginosis, and other bacterial, viral and parasitic infections according to the invention is based on contacting the vaginal epithelium directly with the therapeutic agent. Such direct contact permits an immediate, continuous and efficacious treatment of the treated infections or conditions and eliminates inactivation of the agent by GI tract or by liver metabolism. Such direct treatment also permits use of only such a dosage of the agent as is therapeutically required for treatment of the affected tissue, as in the case of a yeast infection (candidiasis), which is a fungal infection solely of vaginal epithelium. For the uterine infection, the transvaginal treatment also provides general advantages. The transvaginally administered drug is directly transferred from the vagina to the uterus without the need of being digested or processed. The drug is transported to the target organ, namely the uterus, in therapeutic dose which is often only a fraction of a dose administered orally. This manner of administration eliminates secondary symptoms associated with oral or intravenous systemic administration.

A. Treatment of Genital Candidiasis

Genital candidiasis, generally known as yeast infection, is the infection of the genital tract caused by *Candida albicans*, a Gram-positive organism. Women suffering from yeast infection usually develop vulval irritation, itching and vaginal discharge, the vaginal wall is covered with a white cheesy material, vulva is reddish and swollen.

The currently available treatments include orally administered fluconazole and ketoconazole or a locally administered nystatin, clotrimazole or miconazole tablets inserted high into the vagina for 7–14 nights before retiring to prevent leakage of the drug from vagina during the day activity.

The treatment of yeast infection according to the current invention comprises inserting once, twice or as many times/day as needed, a medicated device, preferably a tampon or tampon-like device. The device is medicated with an intravaginal formulation comprising an antifungal agent, such as, butoconazole, fluconazole, ketoconazole, econazole, fenticonazole, tioconazole, terconazole, nystatin, clotrimazole, miconazole, itraconazole and other azole derivatives and antifungal agents as are now known or will become known in the future for their antifungal activities, with a broad spectrum of activity against fungal infections.

The antifungal agent is typically present in amount from about 0.1 to about 2000 mg, preferably from about 1 to about 100 mg per one dose, and most preferably in a dose recommended by PDR and/or drug manufacturer for treatment of candidiasis. The anti-candidiasis formulation is formulated as intravaginal composition comprising essentially a mucoadhesive agent.

B. Treatment of Trichomoniasis

Trichomoniasis is caused by a flagellate anaerobic protozoan *Trichomonas vaginalis*. The trichomoniasis is accompanied by a copious, greenish-yellow, frothy vaginal discharge associated with irritation, itching and soreness of the vulva and thighs. The vaginal walls and cervix surface show punctuate red spots.

The current treatment of trichomoniasis comprises orally administered metronidazole in 2 grams/day dose. This dose may have to be repeated 3 to 5 times in some cases. Alternatively, metronidazole is administered orally in doses of 500 mg twice a day for 7 days. However, because metronidazole is a very potent drug, such large doses may, and have been shown to, cause leukopenia or candidal superinfection. Additionally, metronidazole is available for local treatment of trichomoniasis as a gel formulation to be given for 7 days at bedtime.

The treatment of trichomoniasis according to the current invention comprises inserting intravaginally once, twice or several times/day a device, preferably a tampon or tampon-like device, preferably medicated with a combination of a topical intravaginal and transvaginal formulation comprising an antiprotozoan and/or antifungal and/or antibacterial agent, alone or in any combination, such as, for example, metronidazole and/or clotrimazole and/or clindamycin and any other antiprotozoan, antifungal and/or antibacterial agents as are now known or will become known in the future for their antitrichomonas activities. The antiprotozoan agent is present in amount from about 10 to about 750 mg, preferably from about 50 to about 200 mg per one daily dose. The antibacterial agent is present in amount from about 5 to about 500 mg a day dose. The antifungal agent is present in amount from about 10 to about 500 mg a day dose. Other dosages may be substituted according to PDR recommendation.

The composition typically consists essentially of mucoadhesive agents for intravaginal treatment and, additionally, of penetration enhancer or sorption promoter.

C. Treatment of Bacterial Vaginosis

Bacterial vaginosis is caused by anaerobic bacteria *Gardnerella vaginalis* or *Mycoplasma hominus*. Bacterial vaginosis, also referred to as *Haemophilus vaginitus*, non-specific vaginitis, *Corynebacterium vaginitis* or anaerobic vaginosis typically causes a fishy vaginal odor and thin white vaginal discharge which adheres to the vaginal wall.

The currently available treatment for bacterial vaginosis comprises oral administration of metronidazole 500 mg for several days or oral administration of clindamycin of 600 mg/day. Both metronidazole and clindamycin have been administered intravaginally as a cream or gel as 2% cream or gel comprising 37.5 mg of Metronidazole and 100 mg of clindamycin.

The treatment of bacterial vaginosis according to the current invention comprises inserting once, twice or several times/day a device, preferably a tampon or tampon-like device, preferably medicated with an intravaginal formulation consisting of a mucoadhesive and an antibacterial agent metronidazole and/or clindamycin.

Additionally, if the bacterial infection also affects deep tissues, the treatment comprises administration of transvaginal formulation comprising the mucoadhesive and penetration enhancer agents and the antibacterial agent, such as metronidazole and/or clindamycin and any other antibacterial agent as is now or will become in future known for its antibacterial activity and suitable for treatment of bacterial vaginosis. The antibacterial agent is present in amount from about 5 to about 1000 mg per day dose or in such amount as recommended by PDR.

D. Treatment of Chlamydial Infections

Chlamydial infections are sexually transmitted nongonococcal infections caused by *Chlamydia trachomatis*. These infections include nongonococcal urethritis, mucopurulent cervicitis and nonspecific genital infections. Typically, the affected individual suffers from vaginal discharge, dysuria and cervicitis with yellow, mucopurulent secretion.

The current treatment of chlamydial infections comprises oral administration of broad-spectrum antibiotics, such as tetracycline (2000 mg/day), doxycycline (100 mg/day) or erythromycin (2000 mg/day) for at least 7 days.

For the treatment of the chlamydial infections according to the invention, any known antibiotic which effectively acts upon chlamydial infections is formulated within a device of the invention in an intravaginal and transvaginal formulation comprising from about 10 to about 2000 mg of the antibiotic per daily dose to be delivered transvaginally to the cervix, and through the systemic circulation to other affected organs. The transvaginal formulation comprises a penetration enhancer and/or sorption promoter and/or mucoadhesive agent and may or may not be supplemented with the topical intravaginal formulation depending on the type and extent of the infection.

The antibiotics dose depends on the antibiotic antichlamydial activity and is typically within 100–2000 mg/day dose administered for at least seven days, unless otherwise indicated.

E. Treatment of Gonorrhea

Gonorrhea is a sexually transmitted acute gonococcal infection caused by Neisseria gonorrhoeae. This infection effect epithelium of urethra, cervix, rectum, pharynx and eyes. Typically, the affected female suffers from vaginal discharge, dysuria and cervicitis with purulent or mucopurulent discharge.

Currently, treatment of gonorrhea consists of oral administration of antibiotics in conjunction with anesthetics such as procaine, and adjuvant, such as probenecid. There is no known topical treatment for gonorrhea.

For the transvaginal treatment of gonorrhea according to the invention, known antibiotics are formulated within a device of the invention in a transvaginal formulation which comprises the penetration enhancer, sorption promoter, the mucoadhesive agent and the antibiotic. Antibiotics are lumefloxacin (400 mg), norfloxacin (800 mg), afloxam (400 mg), ciprofloxin (500 mg), azitromycin (1000 mg), cefltoxime (400 mg) and doxycycline (100 mg) twice a day/7 days in doses as needed to alleviate the symptoms and to effectively eliminate gonococcus from the individual organism in daily doses from about 400 mg to about 3000 mg. The formulation may, additionally, contain about 500–1000 mg of probenecid.

F. Treatment of Human Papilloma Virus

Human papilloma virus causes genital warts, a painful and unpleasant condition. The warts are formed on the vaginal wall, the vulva, the cervix and also on perineum. Symptoms include soreness, tenesmus, blood or pus coating, inflammation or ulceration or lesions of the mucosa with mucopurulent secretions.

The current treatment includes electrocauterization, freezing with cryprobe. These treatments often lead to inflammation, lesion healing, ulceration and the pain needs to be treated with topical and systemic drugs.

The treatment according to the invention comprises intravaginal insertion of the soft intravaginal device, such as a foam soaked with a formulation of the invention comprising any drug which is known, or will become known, for treatment of human papilloma virus.

G. Treatment of Genital Herpes

Genital herpes is infection of skin and mucosa of the genital area by herpes simplex virus type 2 and type 1. Symptoms include primary lesions, itching, soreness, erythema, painful vesicles, ulceration and red areola.

The current treatment consists of administration of the oral acyclovir (400 mg 3×/day/7–10 days) and topical administration of acyclovir, famciclovir or valacyclovir.

The topical treatment of genital herpes according to the invention comprises administration of intravaginal and transvaginal preparation of ointment, cream, gel, fluid or powder, preferably incorporated into the intravaginal device. The intravaginal and transvaginal formulation provides contact with the vaginal wall where it treats the epithelium and mucosa herpetic lesions with an antiviral agent combined with, for example, antiprurient agents, emollients and other soothing agents. For eradication of herpes simplex, the antiviral drug, such as acyclovir (200–1200 mg/day), famciclovir (100–1200 mg/day) or famiciclovir (100–1200 mg/day) is administered for at least 7 days in a combination of transvaginal and intravaginal formulation.

II. A Method for Topical Treatment of Infection

The method of the invention, suitable for treatment of fungal, bacterial, viral and parasitic infections and conditions, comprises of inserting into vagina an intravaginal medicated device comprising a drug formulated for treatment of these conditions. The drug may be therapeutically active topically by acting directly on vaginal epithelium or mucosa or it may be transported transvaginally into the uterus, cervix and even into the general circulation.

For each of these three treatments, the drug is formulated differently, as described below. Briefly, the intravaginally active drug is formulated to adhere to and act directly on the vaginal epithelium and mucosa without components which promote its transport or transfer through the vaginal wall. For transvaginal delivery to the uterus and/or to the general circulation, the additives which promote transport and penetration of the drug through the vaginal mucosa are added.

The method for intravaginal treatment is a typical topical treatment comprising contacting the vaginal epithelium directly with the drug for extended periods of time by providing a device comprising a formulation of the drug in combination with at least a mucoadhesive agent to promote adherence of the drug to the vaginal wall.

The method for transvaginal treatment is based on the concept that the upper vagina and the uterus have specific blood flow characteristics, either by a portal type circulation or by venous and lymphatic channels, permitting transport and delivery of the pharmacological agents from the vagina to the uterus and to the blood. This permits higher concentrations of pharmacological agents to be delivered directly to and accumulated in the uterus than can be accomplished by oral administration. This concept has been confirmed in the rabbit model utilizing several drugs as described in U.S. Pat. No. 6,086,909, incorporated herein by reference. The rabbit is the classic model for studying transvaginal drug delivery and extrapolations to people have generally be accepted.

The most specific demonstration of the transvaginal concept has been achieved with the drug ketorolac, a nonsteroidal, non-inflammatory drug, as described in U.S. Pat. No. 6,086,909, but other drugs, when properly formulated, are transported through the vaginal wall similarly.

In general, the method of the invention comprises intravaginal insertion of a medicated device comprising a therapeutic agent for treatment of vaginal, fungal, viral, bacterial or parasitic infection in a pharmaceutically acceptable, non-toxic carrier incorporated into a suitable delivery device which assures the contact with the vaginal mucosa.

The medicated device is applied, that is, inserted intravaginally once, twice or several times a day, as needed, or according to a treatment regimen. The device is typically provided in dry or wet form or may be wetted prior insertion.

The method of the invention provides several advantages over oral administration of drugs or over currently available intravaginal creams or tablets.

First, there is a continuous concentration of drug delivered to the vaginal epithelium and the mucosa to the uterus or to the blood. This provides for higher bioavailability of the drug. Second, there is reduction of first-pass metabolism of the drug in the liver by avoiding the gastrointestinal system. Third, the device of the invention provides a continuous drug depot which allows continuous and uninterrupted delivery of drug to the vaginal epithelium and mucosa over a long period of time. Fourth, and very important, is the reduction of side effects due to avoidance of high concentrations of the drug.

III. Drug Delivery Device and/or System

The vaginal drug delivery device and/or system provides a sustained delivery of the drug to the vaginal epithelium and mucosa for the treatment of vaginal infection or diseases. The delivery system comprises a device such as a tampon, tampon-like device, vaginal ring, pessary, cup, vaginal ring, cervical cup or vaginal sponge, containing a drug in the form of a paste, cream, ointment, microcapsules, solution, powder, or gel having a sufficient thickness to maintain prolonged vaginal epithelium and mucosa contact.

Alternatively, the drug can be incorporated into a coating on a tampon or tampon-like device, sponge, suppository or other absorbent material impregnated with a liquid, drug containing solution, lotion, or suspension of bioadhesive particles, shaped into a tampon-fitting device. The devices of the invention are described in greater detail below in section III. C. Any form of drug delivery system which will effectively deliver the agent to the vaginal epithelium and mucosa or transvaginally through the vaginal mucosa is intended to be included within the scope of this invention.

For purposes of simplifying the description of the invention and not by way of limitation, tampon or tampon-like devices, such as a suppository, for drug delivery will be described hereinafter, it being understood that all effective delivery systems are intended to be included within the scope of this invention.

A. Pharmaceutical Agents

A pharmaceutical agent suitable for intravaginal or transvaginal delivery is any drug which may be formulated into a device according to the invention which is suitable to treat fungal, viral, bacterial and parasitic infections.

Pharmaceutical agents for use in the invention are active on the vaginal epithelium, mucosa or on the uterine epithelium or cervix. The pharmaceutical agent is preferably selected from the group consisting of antifungal, antiviral, antibacterial or antiparasitic agents. Non-limiting examples of anti-fungal drugs suitable for use in the composition of the invention include miconazole, terconazole, isoconazole, fenticonazole, fluconazole, ketoconazole, clotrimazole, butoconazole, econazole, metronidazole, clindamycin, and 5-fluoracil. Anti-viral drugs comprise acyclovir, AZT, famciclovir and valacyclovir. Antibacterial agents suitable for treatment of bacterial vaginosis are metronidazole, clindamycin, ampicillin, amoxicillin, tetracycline, doxycycline and other antibiotics. The anti-trichomonas agent suitable for treatment of trichomoniasis caused by Trichomonas vaginalis is metronidazole.

B. Pharmaceutical Compositions and Formulations

In order to achieve desirable drug release, that is, to act either directly on the vaginal epithelium and mucosa or to be transported through the vaginal wall to the uterus and general circulation, the active ingredient is incorporated into a pharmaceutically acceptable excipient. Any excipient used in formulations of this invention needs to be approved for human use and acceptable for use in the vagina. Excipients approved for oral use may not be approved and/or suitable for vaginal use.

Primary excipients are vehicles or carriers, for which the drug has low affinity. In this respect, hydrophilic drugs are incorporated into lipophilic carriers, and lipophilic drugs are incorporated into hydrophilic carriers.

Preferred lipophilic carriers for use with hydrophilic drugs include any hard fat and/or semi-synthetic glycerides of saturated fatty acids, particularly those having carbon chain of from 8 to 18C. Examples of the lipophilic carrier are SUPPOCIRE® AS2 and related compounds commercially available, for example, from Gattefosse, Westwood, N.J.

Preferred hydrophilic carriers, for promoting synergistic drug delivery, include polyethylene glycol or mixtures thereof, such as PEG 6000/PEG 1500, or PEG 6000/PEG 1500/PEG 400, or PEG 6000/PEG 400, commercially available from, for example, Sigma/Aldrich, St. Louis, Mo.

For intravaginal delivery, the formulation of the invention preferably comprises a mucoadhesive agent to bring the released drug into prolonged, close contact with the mucosal surface. The mucoadhesive agent is preferably a polymer such as an alginate, pectin, or a cellulose derivative. Hydroxypropyl methylcellulose (METHOCEL®) is particularly preferred for use in the present invention.

For transvaginal delivery, the formulation of the invention comprises either the lipophilic or the hydrophilic carrier, (60–90%, by weight), depending on the pharmaceutical agent, the mucoadhesive agent (5–25%, by weight) and additionally includes from about 5–30%, by weight, of a penetration enhancer or sorption promoter to enhance transport and/or permeation of the drug across the uterine mucosal barrier. Preferred sorption promoters and penetration enhancers include nonionic surface active agents, bile salts, organic solvents, particularly ethoxydiglycol commercially available as TRANSCUTOL®, from Gattefosse, (10–30%, by weight) or interesterified stone oil, for example LABRAFIL® M 1944CS, commercially available from Gattefosse.

Preferred formulations for hydrophilic drugs comprise between about 0.1–10%, by weight, of the drug, about 60–90%, by weight, lipophilic carrier, between about 5–25%, by weight, mucoadhesive agent, and between about 5–20%, by weight, sorption promoter.

In a general method for preparing a formulation including a hydrophilic drug, the lipophilic carrier is melted at 45–50° C. in a heated vessel. The mucoadhesive agent is added to the carrier with stirring. The preferred hydrophilic drug is dissolved in the sorption promoter, and the drug/sorption promoter solution is added to the carrier/mucoadhesive agent solution. The final formulation is poured into molds of the desired size and shape or incorporated into a device of the invention, which are then placed in a refrigerator at 4–6° C.

Preferred formulations for the lipophilic drugs comprise between about 0.1–10%, by weight, of the drug, about 50–90%, by weight, hydrophilic carrier, between about 5–20%, by weight, mucoadhesive agent, and between about 5–25%, by weight, sorption promoter. The later added only to transvaginal formulations.

In a general method for preparing a formulation including a lipophilic drug, the hydrophilic carrier is melted in a heated vessel at an appropriate temperature recommended by manufacturer for the particular PEG used. The mucoadhesive agent is added to the carrier with stirring. The preferred lipophilic drug is dissolved in the sorption promoter, and the drug/sorption promoter solution is added to the carrier/mucoadhesive agent solution. The final formulation is poured into molds of the desired size and shape or incorporated into a device of the invention, which are then placed in a refrigerator at 4–6° C.

The drug may be formulated for controlled sustained release. The controlled release drug delivery system must be capable of controlled release of a drug into the vagina over several hours or more. This is achieved by the addition of time release additives such as microcapsules, matrices, etc., known in the art.

During the menstrual cycle, the pH of the vagina changes. Therefore, drug delivery systems additionally may contain buffers to stabilize pH to enhance absorption. Since the delivery system that is the device of the invention must be capable of functioning in the presence of menstrual blood, the blood should be easily removable, for example, by absorption into porous material of a tampon, tampon-like device, the device foam, etc.

Solid phase drug carriers that dissolve or can be diluted can be carried away by menstrual blood. Consequently, the invention preferably provides a device or system that does not dissolve or that is not diluted. The device of the invention is typically a tampon, tampon-like device ring, pessary, cup or foam which has a solid structure into which the intravaginal or transvaginal formulation is incorporated and from which it is released in a timely fashion over a period of time. The time period is typically limited to 2–24 hours, preferably 4–8 hours, which is a hygienically acceptable time to leave the device in place.

Advantages of the medicated intravaginal device include: 1) no increase in messiness; 2) device will not promote bacterial overgrowth with menstrual blood present; 3) device may be washable or reusable, such as, vaginal ring or pessary, 4) continuous delivery of a predictable amount of the drug.

In the preferred embodiment, the delivery system can be a controlled release drug delivery system.

In another preferred embodiment of the invention, the excipient comprises between about 60 to 90% by weight lipophilic carrier, between about 5 to 25% mucoadhesive agent, and between about 5 to 20% penetration enhancer.

In another preferred embodiment of the invention, the excipient comprises between about 60 to 90% by weight hydrophilic carrier, between about 5 to 25% mucoadhesive agent, and between about 5 to 20% penetration enhancer.

In still another preferred embodiment of the invention, the drug delivery system comprises a standard fragrance free lotion formulation sold under the trademark JERGENS® lotion.

In yet another preferred embodiment of the invention, the biocompatible excipient includes glycerin, mineral oil, polycarbophil, carbomer 934P or 940, hydrogenated palm oil, glyceride, sodium hydroxide, sorbic acid, and purified water.

In another preferred embodiment of the invention, the drug delivery system is a vaginal suppository which includes 1–10% of a hydrophilic drug, a lipophilic carrier, 75% SUPPOCIRE® AS2, 10% hydroxypropyl methylcellulose, and 15% TRANSCUTOL®. The suppository may be a stand-alone device or be incorporated into a tampon or tampon-like device.

In another preferred embodiment of the invention, the drug delivery system is a vaginal suppository which includes 1–10% of a hydrophilic drug, a lipophilic carrier, 75% PE6 6000/PEG 1500/PEG 400, 10% hydroxypropyl methylcellulose, and 15% TRANSCUTOL®. The suppository may be a stand-alone device or be incorporated into a tampon or tampon-like device.

C. Devices for Intravaginal Drug Delivery

The controlled release drug delivery system can be in the form of, for example, a tampon, tampon-like device, vaginal ring, vaginal cup, cervical cup, pessary, vaginal sponge, bioadhesive device or bioadhesive device formed of microparticles. The drug is incorporated into these devices as a cream, lotion, foam, solution, paste, ointment, or gel.

In one embodiment, the invention provides a tampon device for delivering a pharmaceutical agent to the uterus comprising an absorbent vaginal tampon having a proximal end and a distal end. A cup-shaped porous foam portion at the distal end fits around the cervix of the uterus and contains a pharmaceutical agent for delivery to the cervix. The device may also include a nonabsorbing axial tube having a distal opening and extending through the porous foam cup into the tampon for conducting blood flow to the absorbent material. Optionally, a retrieval string or tape connected to the tampon device is also included. The absorbent vaginal tampon contains any of the above-mentioned drugs or be coated with the drug and be used as a medicated tampon for individual drug or drug combination delivery.

In another embodiment of a tampon device, the distal porous foam cup has a rim which encircles the cervix. The rim has high concentrations of medication and is positioned away from the direct flow of blood which exudes from the cervix during menstruation.

In another embodiment of a tampon device, the distal porous foam cup has a rim which encircles the cervix. The rim has fingers extending into the fornix areas around the cervix and the tips of the fingers have high concentrations of medication and are positioned away from the direct flow of menstrual blood.

In another embodiment of a tampon device, a distal porous foam section is in the shape of a scoop, which only partially encircles the cervix. The porous foam scoop has a nib-like shape which is designed to wedge itself into the posterior fornix. The porous foam scoop is designed to deliver medication to the vaginal wall along the entire length of the porous foam scoop.

In another embodiment, a tampon device is sheathed in a thin, supple, non-porous material such as a plastic film or a coated gauze that surrounds the absorbent tampon material like a skirt and opens like an umbrella when it comes in contact with the vaginal environment. A band of drug, ideally suspended in a wax-like carrier that melts at body temperature, encircles the sheathed tampon. Contact with vaginal fluids or menstrual flow causes the tampon to swell, forcing the skirt to open like an umbrella and to press tightly against the vaginal wall, putting the drug in contact with the vaginal mucosa while effectively preventing the drug from being absorbed into the tampon.

In another embodiment of a tampon device, distal fibers of the tampon which contact the cervix have high concentrations of pharmaceutical agent for delivery of the agent to the cervical tissue.

In another embodiment of a tampon device, the tampon device has an outer tubing having perforations, the outer tubing is concentric around an axial tube. The device has a distal porous foam section which in its dehydrated state is tight around the outer tubing. A bladder is located proximally to the porous foam and filled with liquid pharmaceutical agent. The bladder is connected to the outer tubing. An outer sheath covers the tampon. The sheath has an annular constriction distal to the bladder such that deployment of the tampon through the distal end of the sheath causes the liquid in the bladder to be forced out distally through the perforated outer tubing and into the porous foam.

In another embodiment of a tampon device, the tampon device has an annular delivery composition around the distal end. The composition contacts the vaginal epithelium for delivery of the agent. A non-absorbing axial tube opens distally and extends into the tampon for conducting blood flow to the absorbent material proximal to the porous foam. The annular composition can be a suppository, foam, microparticles, paste, or gel.

Embodiments of the invention may include tampon devices of a standard length, or may be longer or shorter than standard tampons to facilitate positioning the tampon device closer to or in contact with the vaginal wall or with the cervix.

Particular device embodiments of the invention are described in greater detail in FIGS. 1–19. FIGS. 1 and 2 show anatomical arrangement of the vagina, uterus and other organs. FIGS. 3–19 show various devices inserted into the vagina.

FIG. 1 is a cross-sectional representation of a portion of the female reproductive organs, including the uterus 2 and the vagina 8 in the upright orientation.

FIG. 2 is a cross-sectional side view representation thereof. The uterus 2 is a muscular organ enclosing the womb 4, and opening at the cervix 5 via the cervical canal or cervical of 6. The vagina 8 is defined by a muscular tube 10 leading from the labia minora 12 and labia majora 14 to the cervix 5.

FIG. 3 is a cross-sectional representation of FIG. 1 showing placement of a drug delivery system 16 in the vagina 8 which drugs are introduced intravaginally to the vaginal wall 10 or transvaginally to the uterus 2 by way of the vaginal blood vascular and lymphatic systems.

Referring now to FIGS. 4–12, there being depicted various embodiments of tampon-like devices which can be used to deliver drugs for treatment of vaginal infections according to the invention. If a tampon-like device is used, there are numerous methods by which a drug can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. This arrangement permits simultaneous drug delivery from the upper part of the device and absorption of the discharge or menstrual blood in the lower porous part of the tampon or tampon-like device. Alternatively, the drug can be incorporated into an insertable suppository which is placed in association with the tip of the tampon.

The tampon-like device can be constructed so as to improve drug delivery. For example, the tampon can be shaped to fit in the area of the posterior fornix and pubic symphysis and constructed so as to open up to have maximum surface area of contact for drug delivery. If the drug is in a reservoir on the surface of the device, the shape of the device should be such that it can maintain the reservoir towards a vaginal mucosal orientation for best predictable drug release characteristics.

The tampon device can also be constructed so as to have a variable absorption profile. For example, the drug area at the tip of the tampon device could be different from that of the more proximal area in order to force the drug to diffuse out into tissue, as opposed to down into the absorbent part of the tampon. Alternatively, there could be a non-absorbing channel around the cervix for the first centimeter or so in order to minimize menstrual flow from washing away the drug composition.

The release of drug from the tampon device should be timed to provide proper uterine concentration of the drug over a typical length of use of a tampon device, usually 1–8 hours.

FIG. 4 is a cross-sectional representation of the vaginal area, adjacent the cervix 5, with a first embodiment of a tampon drug delivery system according to the invention. The tampon device 22 comprises an absorbent cylindrical tampon 24 comprised of fibrous material, for example cotton, having around its distal end 26 an annular delivery composition 28. The tampon device 22 places the annular delivery composition 28, supported around the distal end 26 of the tampon device 22, against the upper epithelium 18 of the vagina 8 and posterior fornix 20 for delivery through the vaginal surfaces in which the annular composition 28 is in contact. The annular composition 28 can be an annular suppository, foam, paste, or gel composed of suitable delivery components. The uterine discharge is absorbed by the tampon 24 and is prevented from carrying away the treatment composition.

FIG. 5 is a cross-sectional representation of the vaginal area adjacent the cervix 5 with a second embodiment of a tampon drug delivery system according to the invention. In this embodiment, tampon device 32 includes a non-porous tube 34 which communicates with the cervical of 6 for delivery of the menstrual discharge from the cervical of to an absorbent cylindrical tampon 36 comprised of fibers, for example cotton, for absorbing the discharge. The tube 34 prevents contact of the discharge with an annular drug delivery composition 38.

FIG. 6 is a cross-sectional representation of the vaginal area adjacent the cervix 5 with a third embodiment of a tampon drug delivery system according to the invention. In FIG. 6, the tampon device 42 includes a distal porous foam section 43 which is in the shape of a cup in the expanded state. In the center of the porous foam section 43 is a non-porous tube 44 which will conduct blood flow to absorbent tampon 45 proximal to the porous foam section 43. The porous foam is preferably a soft, light weight, physiologically inert foam material of polyurethane, polyester, polyether, such as described in U.S. Pat. No. 4,309,997, or other material such as collagen as described in U.S. Pat. No. 5,201,326, both incorporated herein by reference. The axial tube is preferably a non-absorptive physiologically inert material, such as rubber or plastic, and can be coated on its inner surface with an anticoagulant. The proximal end 46 of the tube 44 has a plastic loop 47 to which a string 48 may be tied for removal of the tampon device 42. The cup-shaped porous foam section 43 fits around the cervix 5 of the uterus 2 and contains medication which may be delivered to the cervical tissue.

FIG. 7 is a cross-sectional representation of the vaginal area adjacent the cervix 5 with a fourth embodiment of a tampon drug delivery system according to the invention. In FIG. 7, the tampon device 52 includes a distal porous foam cup 54 and a proximal absorbent tampon 56. The porous foam cup 54 has a rim 58 which encircles the cervix 5, and which contains high concentrations of medication. The rim 58 area of the porous foam cup 54 is away from the direct flow of blood. The tampon device 52 includes a string 59 for removal of the tampon device 52. FIG. 7A is a cross-sectional view of the embodiment shown in FIG. 7, taken in the direction indicated by the arrows labeled 7A in FIG. 7. As illustrated in FIG. 7A, the rim 58 area forms a ring which contains a high concentration of medication. Alternatively, as illustrated in FIG. 8, the entire porous foam cup 55 may contain medication, not just in the ringed tip area 59 near the cervix 5.

FIG. 9 is a cross-sectional representation of the vaginal area adjacent the cervix 5 with a fifth embodiment of a tampon drug delivery system according to the invention. In FIG. 9, the tampon device 62 includes a proximal absorbent tampon 64 and a distal section 66 which includes a dissolvable suppository or gel capsule 67 filled with liquid medication. The medication prior to dissolution or release of the liquid has a "doughnut" shape to allow for blood to pass through the center of the tampon 64. The tampon device 62 includes a string 68 attached to the tampon 64 for removal of the tampon device 62. FIG. 9A is a cross-sectional view of the of the embodiment shown in FIG. 9, taken in the direction indicated by the arrows labeled 9A in FIG. 9, and illustrates the doughnut shape of the medication filled suppository or gel capsule 67.

FIG. 10 is a cross-sectional representation of the vaginal area adjacent the cervix 5 with a sixth embodiment of a tampon drug delivery system according to the invention. In FIG. 10, the tampon device 72 includes a porous foam distal section 74 which is in the shape of a cup with "fingers" 76 which extend into the fornix areas 20 around the cervix 5. The tips of the fingers 76 contain high concentrations of medication which may be delivered to areas away from the direct flow of blood or discharge as the blood or discharge moves into absorbent tampon 78 proximal to the cup-shaped porous foam distal section 74. The tampon device 72 includes a string 79 for removal of the tampon device 72. FIG. 10A is a side view of the porous foam cup 74 and illustrates the fingers 76 which extend into the fornix areas 20 around the cervix 5 (FIG. 10).

It will be readily apparent to a person skilled in the art that the characterization of the drug delivery device as having an annular shape is only an approximate description of the shape formed by fluid or semisolid drug delivery devices positioned around a cylinder and in contact with adjacent vaginal wall epithelium, and all shapes which conform to the vaginal epithelium and external cervical surfaces are intended to be included within and indicated by the term "annular". Moreover, use of the term "annular" does not restrict the invention to the use of such devices which encircle the entire cervix (i.e. 360 degrees). Devices which span an angle of less than 360 degrees, but which make sufficient contact with the vaginal epithelium to deliver sufficient quantity of the drug are within the scope of the invention.

The annular drug delivery composition (FIG. 4 or 5) can be an absorbent material which expands in the presence of fluid or body heat to completely fill the space between the tampon 22, 32 and the vaginal epithelium 18.

Figure 11:
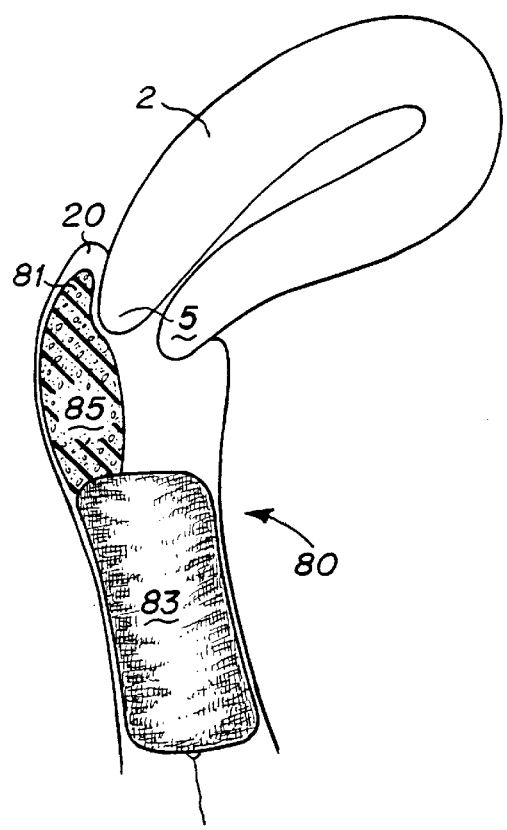
FIG. 11 is the representation of FIG. 2 showing placement of a tampon device incorporating a scoop-shaped distal porous foam section.
Figure 12:
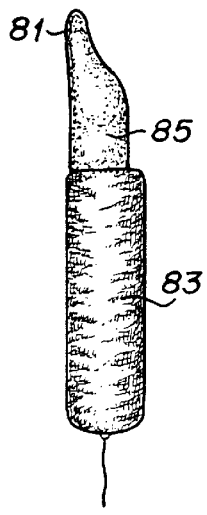
FIG. 12 is a side view of the embodiment shown in FIG. 11.
Figure 13:
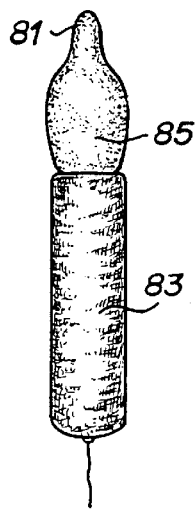
FIG. 13 is a front view of the embodiment shown in FIG. 11.

FIG. 11 illustrates such a drug delivery device having an annular shape which does not completely encircle the entire cervix. FIG. 11 is the representation of FIG. 2 showing placement of a seventh embodiment of a tampon device 80 incorporating a scoop-shaped porous foam section 85. FIG. 12 is a side view of the tampon device 80 and FIG. 13 is a front view of the tampon device 80. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver medication to the vaginal wall along the entire length of the scoop-shaped porous foam section 85.

Figure 14:
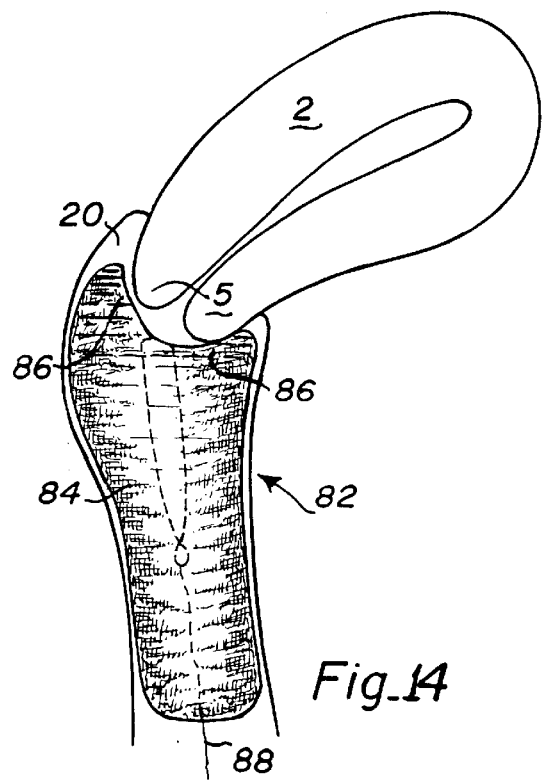
FIG. 14 is the representation of FIG. 2 showing placement of a tampon-like device incorporating distal fibers containing concentrated medication.

FIG. 14 is a cross-sectional representation of the vaginal area adjacent the cervix 5 with an eighth embodiment of a tampon drug delivery system according to the invention. In FIG. 14, the tampon device 82 comprises an absorbent tampon 84. The section 86 of the tampon 84 which rests against the cervix 5 contains high concentrations of medication. As the fibers absorb fluid, the tampon 84 expands around the cervix 5 and delivers medication to the tissue. The blood will be drawn to proximal sections of the tampon 84 as fibers become more absorbent in this area. The tampon device 82 includes a string 88 for removal of the tampon device 82.

Suitable cylindrical cartridge containers or inserter tubes which assist in the insertion and storage of the tampon systems of the present invention will be apparent to those skilled in the art of tampon construction. Examples are described in U.S. Pat. Nos. 4,3178,447; 3,884,233; and 3,902,493, incorporated herein by reference.

In general practice, a drug delivery tampon device as described herein is placed into the vagina and the inserter tube is removed. The tampon device contacts the inner wall of the vagina where the mucoadhesive agents facilitate adhesion of the drug released from the device to the vaginal wall where it is therapeutically effective. For transvaginal delivery, the penetration enhancers and mucoadhesive agents act to facilitate the adhesion of the drug to the vaginal mucosa and/or adsorption of the drug into the local vasculature. This results in a higher concentration of the drug being delivered to the uterine muscle where it acts to treat vaginal or uterine infections or uterine conditions.

Figure 15:
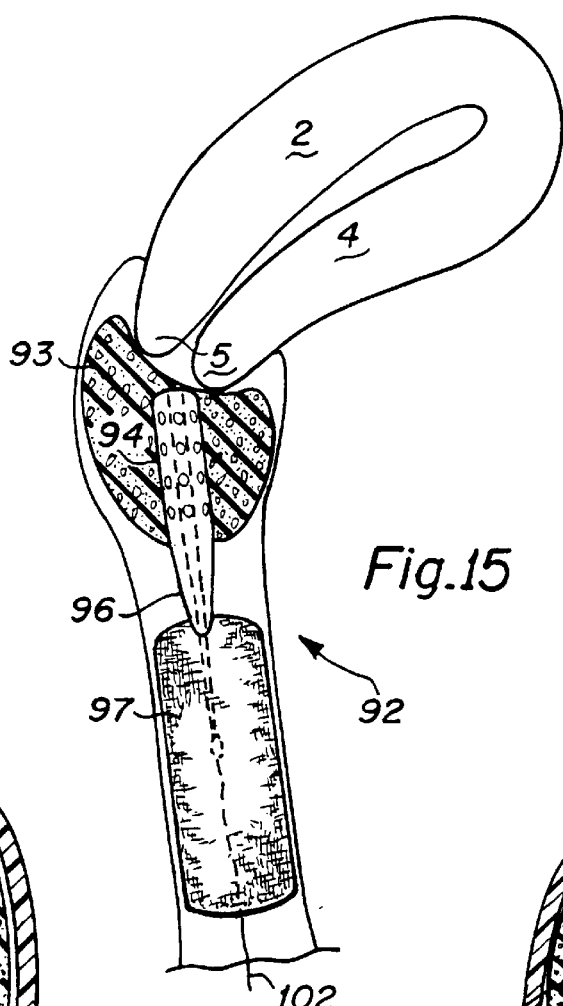
FIG. 15 is the representation of FIG. 2 showing placement of a tampon-like device incorporating non-absorbent tubing having a distal opening.
Figure 16:
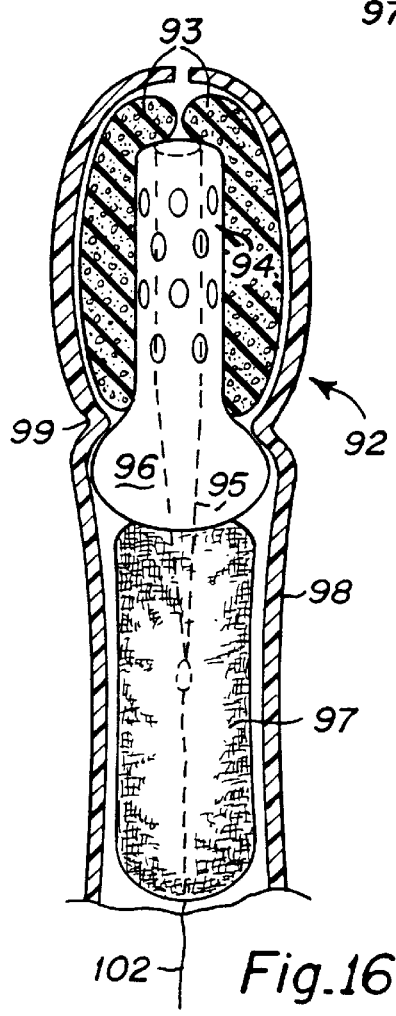
FIG. 16 is the tampon drug delivery system of FIG. 15 in a dehydrated and sheathed state.
Figure 17:
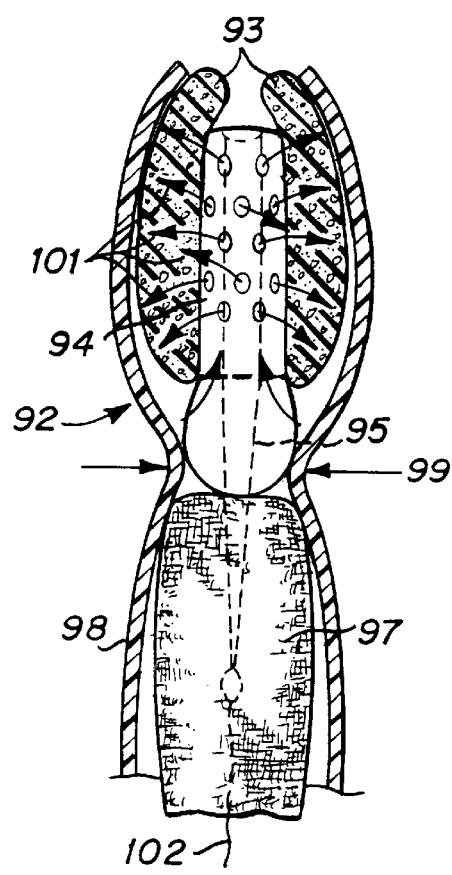
FIG. 17 is the tampon drug delivery system of FIG. 16 showing deployment of the tampon.

FIG. 15 is a cross-sectional representation of the vaginal area adjacent the cervix 5 with another embodiment of a tampon drug delivery system according to the invention. In FIG. 15, the tampon device 92 includes a distal porous foam section 93 which, in its dehydrated, sheathed state (FIG. 16), is tight around a perforated outer tube 94. The perforated outer tube 94 is connected to a bladder 96 located proximally which is filled, for example, with liquid medication. Within the perforated outer tube 94 is a concentric inner tube 95 which provides a pathway for blood to flow into an absorbent tampon 97 which is proximal to the porous foam section 93. Prior to insertion, the tampon device 92 is enveloped in a sheath 98 which is necked down at site 99 between the porous foam section 93 and the bladder 96 so that, when the tampon device 92 is deployed and the sheath 98 moves over the bladder 96, the medication is forced out seen as 101, through the perforated outer tube 94 into the porous foam section 93 (FIG. 17). The tampon device 92 includes a string 102 for removal of the tampon device 92.

Figure 18A:
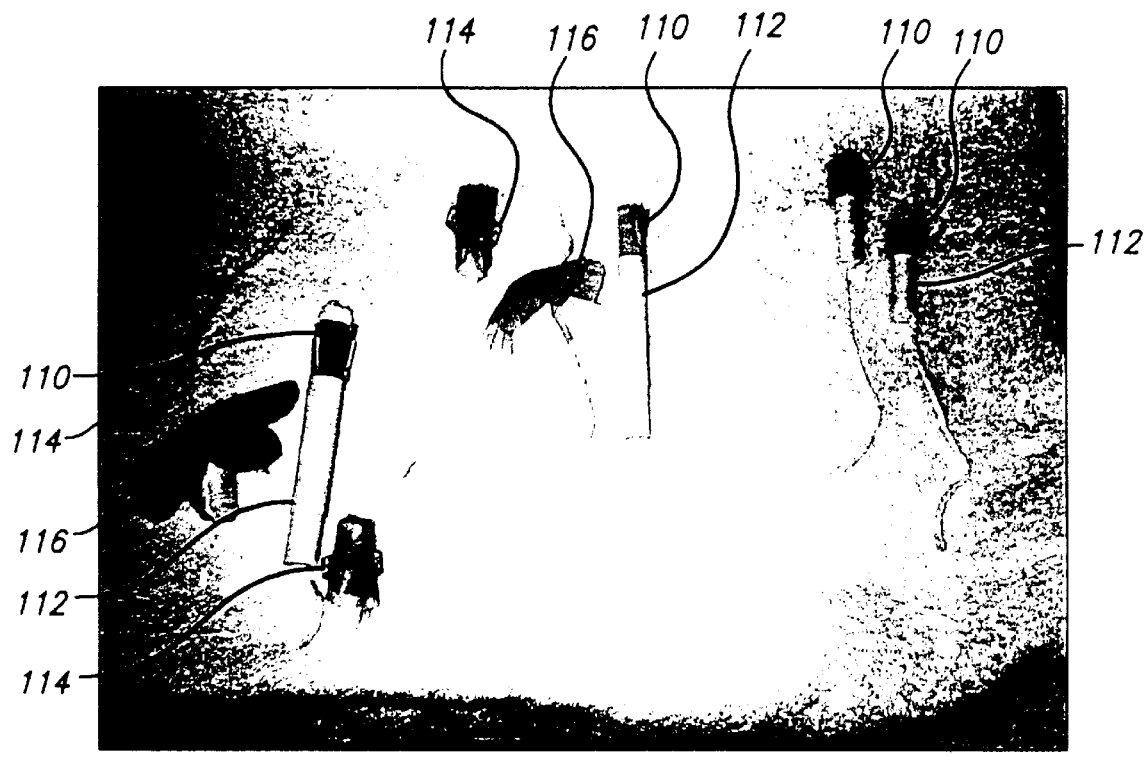
FIGS. 18A and 18B show several configurations of a sheathed tampon of the skirt and umbrella design; with and without medication, both in and out of a cardboard applicator, and in expanded form to simulate device appearance after use.
Figure 18B:

FIG. 18A and 18B show an alternative tampon-like device of a skirt and umbrella design, wherein the tampon packaged for use is sheathed in a nonporous gauze-like material attached to the proximal end of a tampon in skirt-like fashion (110) with a band encircling the device, said band comprising the drug formulated in SUPPOCIRE®, PEG or another carrier configuration and, depending whether the intended drug delivery is intravaginal or transvaginal, further comprising a mucoadhesive and/or sorption promoter. Tampon with skirt and medication fits into a standard cardboard device (112) used for vaginal insertion. When the tampon is inserted into the vagina, the skirt 110 opens up in the umbrella like fashion. The open umbrella pushes the medicated surface band against the vaginal mucosa and as the tampon absorbs vaginal moisture, discharge and menstrual flow it swells to hold the outer surface of the tampon tightly against the mucosal surface. The skirt is typically made of a plastic film similar to cling wraps or bags used in food storage but may be made of any thin, supple nonporous material such as a cloth or gauze, plastic, or cloth or plastic netting material, such as soft organza, tulle or cotton including those that are nonporous due to a coating. Any other suitable material may be used as the skirt material.

Figure 19:
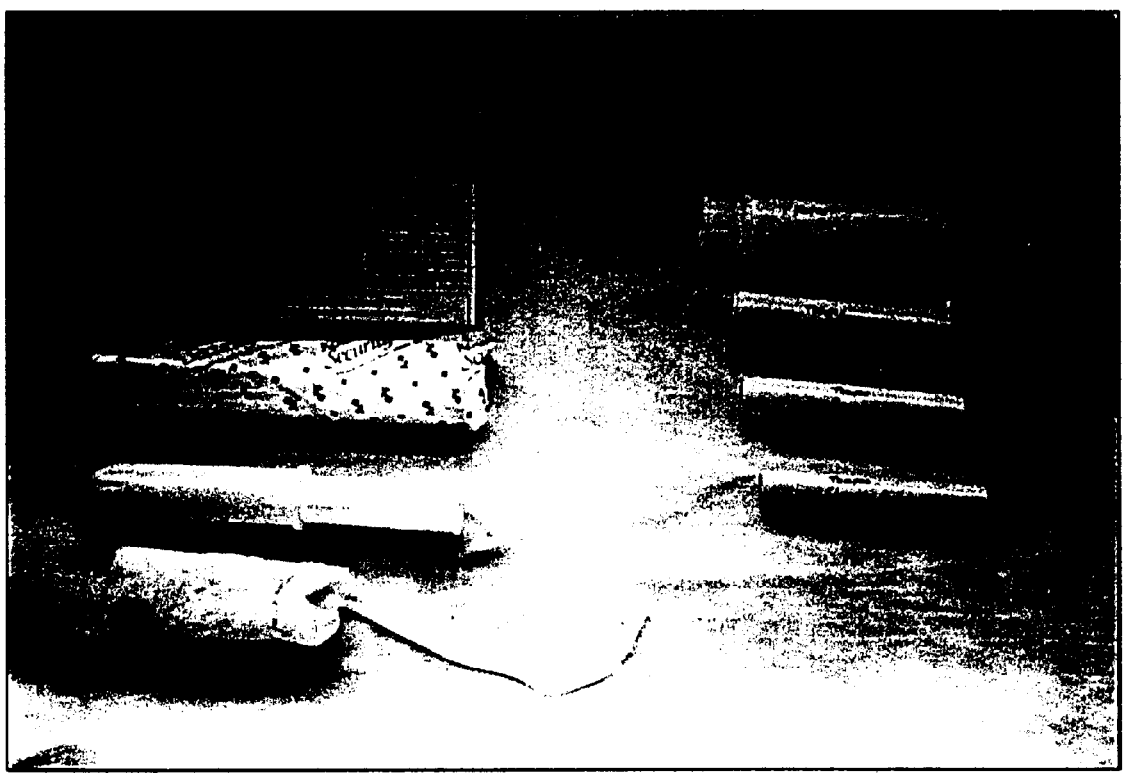
FIG. 19 illustrates the different sizes and styles of tampon inserters currently on the market, the cardboard tube inserters on the right are most appropriate for the FIG. 18 design.

FIG. 19 shows a typical plastic inserter design (left) with a tapered tip, which is readily useable for the sheathed tampon device. The cardboard inserters on the right have a wide, open tip that is not likely to dislodge the sheath and medication. Cardboard applicators are available in a variety of sizes, making adaptation of current tampon configurations easily accomplished.

Another example of a suitable controlled release drug delivery system for the present invention is the vaginal ring. Vaginal rings usually consist of an inert elastomer ring coated by another layer of elastomer containing the drug to be delivered. The rings can be easily inserted, left in place for the desired period of time, up to 7 days, then removed by the user. The ring may be solid or hollow containing the drug or it may be a porous material releasing the drug therefrom. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

Pessaries, cervical cups, tablets and suppositories are other examples of drug delivery systems which can be used in the present invention. These systems have been used for delivery of vaginal contraceptives, and have been described extensively in the literature.

Another example of a delivery system is the vaginal sponge. The desired pharmaceutical agent can be incorporated into a silicone matrix which is coated onto a cylindrical drug-free polyurethane vaginal sponge, as described in the literature.

Bioadhesive tablets are another drug delivery system. These bioadhesive systems use hydroxypropyl cellulose and polyacrylic acid. They release drugs for up to five days once they are placed in the appropriate formulation. The tablet of the invention will have the shape of a suppository or a tampon so that the maximum contact is achieved between the vaginal wall and the tablet surface.

Bioadhesive microparticles constitute still another drug delivery system suitable for use in the present invention. This system is a multi-phase liquid or semi-solid preparation which does not seep from the vagina as do most current suppository formulations. The substances cling to the wall of the vagina and release the drug over a several hour period of time. Many of these systems were designed for nasal use, such as U.S. Pat. No. 4,756,907, incorporated herein by reference, but can be advantageously used on the vaginal mucosa. The system may comprise microspheres with an active drug and a surfactant for enhancing uptake of the drug. The microparticles have a diameter of 10–100 pm and can be prepared from starch, gelatin, albumin, collagen, or dextran by methods known in the art.

The drug can also be incorporated into creams, lotions, foams, paste, ointments, and gels which can be applied to the vagina using an applicator. Processes for preparing pharmaceuticals in cream, lotion, foam, paste, ointment and gel forms were discussed above and can be found throughout the literature. An example of a suitable system is a standard fragrance free lotion formulation containing glycerol, ceramides, mineral oil, petrolatum, parabens, fragrance and water such as the product sold under the trademark JERGENS® (Andrew Jergens Co., Cincinnati, Ohio). The use of this formulation was described in Abstract No. 97.051, North American Menopause Society, Boston, Mass., Sept. (1997), incorporated herein by reference, for transcutaneous delivery of estradiol and progesterone.

Suitable nontoxic pharmaceutically acceptable excipients for use in the compositions of the present invention will be apparent to those skilled in the art of pharmaceutical formulations and examples are described in *REMINGTON'S Pharmaceutical Sciences*, 19<sup>th</sup> Edition, A. R. Gennaro, ed., (1995). The choice of suitable carriers will depend on the exact nature of the particular vaginal dosage form desired, e.g., whether the active ingredient(s) is/are to be formulated into a cream, lotion, foam, ointment, paste, solution, or gel, as well as on the identity of the active ingredient(s).

Although the compositions described above typically contain only one pharmaceutically active agent for treatment of fungal, viral, bacterial or parasitic infections, such compositions may additionally contain other pharmaceutical agents or a combination thereof, such as, for example, pain killers, antipruritics, corticosteroids and other agents which may enhance the therapeutic effect of the primary drug.

In practice, the drug delivery systems of the invention are applied upon appearance of symptoms of vaginal or uterine infections. Typically, the treatment is continued for a few hours up to 14 days, or as needed, to alleviate and prevent painful infections of the vagina and uterus.

Other features of the invention will become apparent in the course of the following descriptions of exemplary embodiments which are given for illustration of the invention and are not intended to be limiting thereof.

EXAMPLE 1

Preparation of Drug Containing Vaginal Tampon-like Device for Transvaginal Delivery This example describes a process for preparation of tampon for transvaginal delivery of amoxicillin.

Amoxicillin (250 mg) obtained from Sigma/Aldrich, St. Louis, Mo. was mixed with radioactively labeled $^3$H amoxicillin (4–7 $\mu$Ci). Vaginal suppositories were formulated and prepared 24 hours prior to each use.

The three basic ingredients for the amoxicillin formulation were the lipophilic carrier SUPPOCIRE® AS2 obtained from Gattefosse, Westwood, N.J. (75%/wt); a mucoadhesive hydroxypropyl methylcellulose (e.g. METHOCEL® K, HPMC K15M) obtained from Dow Chemical, Midland, Mich., (10%/wt); and penetration enhancer TRANSCUTOL® obtained from Gattefosse (15%/wt). These ingredients were mixed in percent amounts as shown. To make eight suppositories, 4.5 grams of SUPPOCIRE, 600 mg of HPMC, 900 mg of TRANSCUTOL, the calculated dose of the drug (250 mg/suppository), and its labeled counterpart were weighed out. SUPPOCIRE was melted in a disposable 100 mL polypropylene beaker suspended in water at 50° C. The solution was stirred until completely melted. HPMC and TRANSCUTOL were then added and mixed. Finally, the unlabeled drug and the radioactively-labeled drug were added to the warm solution. The warm mixture was quickly poured into TYGON® tubing (available from Fisher Scientific, Pittsburgh, Pa.) molds (2×0.5 cm dimensions), the tubing was kept upright on an ice-cold glass slab. Suppositories were kept refrigerated until use. The suppository was weighed prior to each experiment to determine the actual drug dose.

The prepared suppository was then incorporated into a vaginal tampon according to the invention in such a way that the drug was released from the tip of the suppository in a sustained time-release manner.

In an alternative arrangement, the tampon was soaked in the formulation comprising 250 mg of ampicillin, dried and protected by the carton inserter until used.

EXAMPLE 2

Preparation of a Gel Containing Metronidazole For Intravaginal Application

This example describes the preparation of intravaginal formulation for treatment of trichomoniasis.

250 mL of isotonic saline was heated to 80° C. and 1.5 grams of METHOCEL® were added, with stirring. The resultant mixture was allowed to stand at room temperature for 2 hours. Then 150 mg of metronidazole was mixed together with 250 mg of clindamycin and 10 mg of Tween 80 was added. The mixture was stirred and a quantity of isotonic saline sufficient to bring the total volume to 500 mL were added to the gel. All ingredients were thoroughly mixed and let stand until the gel was formed.

The gel was incorporated into the porous vaginal sponge for release through the pores upon contact with the vaginal wall.

EXAMPLE 3

Preparation of Acyclovir Containing Lotion for Intravaginal Application

Acyclovir (50 mg/1 ml) obtained from Sigma/Aldrich, St. Louis, Mo., was added to one ml of JERGENS® standard fragrance free lotion. The lotion was incorporated into the tampon for intravaginal delivery.

EXAMPLE 4

Preparation of Metronidazole Containing Gel for Intravaginal Application

Metronidazole (7.5 mg/g of gel) obtained from Sigma/Aldrich, St. Louis, Mo., was added to one gram of gel comprised of the following ingredients: glycerin, methyl and propyl parabens, mineral oil, polycarbophil, carbomer 940 934P, propylene glycol, hydrogenated palm oil, glyceride, sodium hydroxide, sorbic acid, edelate disodium and purified water. The gel was incorporated into the vaginal tampon.

EXAMPLE 5

Preparation of Vaginal Suppositories

A vaginal suppository is prepared for intravaginal administration of each one of the following drugs at the indicated dose: miconazole (100 mg), terconazole (80 mg), isoconazole (80 mg), fenticonazole (100 mg), fluconazole (150 mg), ketoconazole (200 mg), clotrimazole (100–500 mg), butoconazole (2%), econazole, metronidazole (150 $\mu$g), clindamycin (100 mg), 5-fluoracil (50 mg), acyclovir (400 mg), AZT or famovir (250 mg).

All of the steps in the preparation of the drug suppository are identical to those of Example 1 except that no radiolabeled compound is used and the indicated amount of drug is used in place of ampicillin.

The quantity of vaginal dosage form needed to deliver the desired dose will of course depend on the concentration of the active ingredient in the composition. The therapeutic dosage range for vaginal administration of the compositions of the present invention will vary with the size of the patient, the severity of symptoms and regimen prescribed by the physician.

EXAMPLE 6

Preparation of Vaginal Medicated Tampons For Treatment of Candidiasis

The tampon or other vaginal device is prepared by incorporating an intravaginal formulation comprising hydroxymethyl cellulose, lipophilic carrier and, if desired, also a sorption promoter. The formulation comprises an antifungal agent selected from butoconazole, fluconazole, ketoconazole, econazole, fenticonazole, tioconazole, terconazole, nystatin, itraconazole, clotrimazole, or miconazole formulated as a cream, ointment, powder, solution, suspension, gel, foam or emulsion and added to the material either before the tampon is fabricated or the prefabricated tampon is soaked in the solution, suspension, emulsion or other fluid preparation.

The amount of the drug is between 0.1 and 2000 mg, such that it assures that the dose administered by vaginal tampon is at least as high (600 mg) as the one indicated in PDR for Monistat (miconazole) and is delivered to the vaginal mucosa in a dose linear manner.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A medicated intravaginal device for delivery of an antifungal, antiviral, antibacterial, trichomonicidal or parasiticidal pharmaceutical agent intravaginally to a female vagina or transvaginally to uterus or general circulation through a vaginal mucosa, said device comprising a vaginal tampon, vaginal ring, vaginal cup, vaginal tablet, vaginal sponge, or vaginal bioadhesive tablet incorporated with a composition comprising from about 0.1 to about 10%, by weight, the antifungal agent, selected from the group consisting of miconazole, terconazole, isoconazole, fenticonazole, fluconazole, nystatin, ketoconazole, clotrimazole, butoconazole, econazole, tioconazole, itraconazole, 5-fluoracil and metronidazole, or the antiviral agent selected from the group consisting of acyclovir, femciclovir, valacyclovir and AZT, or the antibacterial agent selected from the group consisting of clindamycin, tetracycline, amoxicillin, ampicillin, erythromycin, doxycycline, lumefloxacin, norfloxacin, afloxam, ciproflaxin, azitromycin and cefltoxine present in amount from about, or the antichlamydial agent selected from the group consisting of tetracycline, doxycycline and erythromycin; or the trichomonicidal or parasiticidal agent selected from the group consisting of metronidazole and clotrimazol, or a combination thereof, said pharmaceutical agent in admixture with a pharmaceutically acceptable, non-toxic excipient comprising from about 60 to about 90%, by weight, of lipophilic or hydrophilic carrier and from about 5 to about 25%, by weight, of mucoadhesive agent for intravaginal delivery, or from about 60 to about 90%, by weight, of lipophilic or hydrophilic carrier, from about 5 to about 25%, by weight, of mucoadhesive agent and from about 5 and 20%, by weight, of penetration enhancer or sorption promoter for transvaginal delivery.

2. The device of claim 1 incorporated with a composition wherein the lipophilic carrier is a semi-synthetic glyceride of saturated fatty acids of 8–18 carbon atoms, wherein the hydrophilic carrier is polyethylene glycol of a molecular weight from 400 to 6000, wherein the mucoadhesive agent is alginate, pectin or hydroxypropyl methylcellulose; and wherein the penetration enhancer or sorption promoter is a surfactant, bile salt or ethoxyglycol.

3. The device of claim 2 incorporated with a composition comprising about 60 to about 90%, by weight, the polyethylene glycol, about 5 to about 20% of hydroxypropyl methylcellulose, about 5 to 30%, by weight, of ethoxyglycol.

4. The device of claim 3 incorporated with a composition for treatment of candidiasis comprising the antifungal agent selected from the group consisting of miconazole, terconazole, isoconazole, fenticonazole, fluconazole, nystatin, ketoconazole, clotrimazole, butoconazole, econazole, tioconazole, itraconazole, 5-fluoracil and metronidazole, or a combination thereof, present in amount from about 0.1 to about 2000 mg.

5. The device of claim 4 wherein said antifungal agent is ketoconazole incorporated into the tampon.

6. The device of claim 4 wherein said antifungal agent is miconazole incorporated into the tampon.

7. The device of claim 3 incorporated with a composition for treatment of trichomoniasis comprising metronidazole present in amount from about 10 to about 750 mg.

8. The device of claim 7 wherein metronidazole is incorporated into the tampon.

9. The device of claim 3 incorporated with an antibacterial composition for treatment of bacterial vaginal infections comprising the antibacterial agent selected from the group consisting of clindamycin, tetracycline, amoxicillin, ampicillin, erythromycin, doxycycline, lumefloxacin, norfloxacin, afloxam, ciproflaxin, azitromycin and cefltoxine, or a combination thereof, present in amount from about 5 to about 1000 mg.

10. The device of claim 9 wherein said antibacterial agent is tetracycline, doxycycline, azithromycin or erythromycin incorporated into the tampon.

11. The device of claim 3 incorporated with a composition for treatment of gonorrhea or chlamydial infections comprising a broad spectrum antibiotic agent selected from the group consisting of clindamycin, tetracycline, amoxicillin, ampicillin, erythromycin, doxycycline, lumefloxacin, norfloxacin, afloxam, ciproflaxin, azitromycin and cefltoxine, or a combination thereof, present in amount from about 100 to about 3000 mg.

12. The device of claim 11 incorporated with a composition for treatment of gonorrhea wherein said antibiotic agent is tetracycline, amoxicillin, ampicillin, lumefloxacin, norfloxacin, afloxam, ciproflaxin, azitromycin or cefltoxine, or a combination thereof, present in amount from about 400 to about 3000 mg and wherein the device is the tampon.

13. The device of claim 3 incorporated with a composition for treatment of chlamydial infections comprising tetracycline, doxycycline and erythromycin in amount from about 100 to about 2000 mg and wherein the device is the tampon.

14. The device of claim 3 incorporated with a composition comprising the antiviral agent selected from the group consisting of acyclovir, femciclovir, valacyclovir and AZT, or a combination thereof, in amount from about 100 to about 1200 mg.

15. The device of claim 14 wherein said antiviral agent is acyclovir incorporated into the tampon.

16. The device of claim 3 wherein said composition comprising said pharmaceutical agent is incorporated into the device as a controlled release drug delivery system.

17. The device of claim 3 wherein said composition is incorporated into said tampon, vaginal ring, vaginal cup, vaginal tablet, vaginal sponge or vaginal bioadhesive tablet as a cream, lotion, foam, ointment or solution.

18. The device of claim 3 wherein said composition is incorporated into said tampon, vaginal ring, vaginal cup, vaginal tablet, vaginal sponge or vaginal bioadhesive tablet as a gel.

* * * * *